(12) United States Patent
Ackley et al.

(10) Patent No.: US 8,567,232 B2
(45) Date of Patent: Oct. 29, 2013

(54) GAS SENSOR USING NANOTUBES

(75) Inventors: H. Sprague Ackley, Seattle, WA (US); Christopher A. Wiklof, Everett, WA (US)

(73) Assignee: Empire Technology Development LLC, Wilmington, DE (US)

( * ) Notice: Subject to any disclaimer, the term of this patent is extended or adjusted under 35 U.S.C. 154(b) by 284 days.

(21) Appl. No.: 12/997,859

(22) PCT Filed: Jul. 9, 2010

(86) PCT No.: PCT/US2010/041572
§ 371 (c)(1),
(2), (4) Date: Dec. 13, 2010

(87) PCT Pub. No.: WO2012/005738
PCT Pub. Date: Jan. 12, 2012

(65) Prior Publication Data
US 2012/0006096 A1   Jan. 12, 2012

(51) Int. Cl.
*G01N 29/02* (2006.01)
*G01N 33/00* (2006.01)

(52) U.S. Cl.
CPC .................................. *G01N 33/0055* (2013.01)
USPC ........................ 73/24.01; 73/24.06; 324/633

(58) Field of Classification Search
USPC ............ 73/24.01, 31.01, 24.02, 24.03, 24.04, 73/24.05, 24.06; 324/633
See application file for complete search history.

(56) References Cited

U.S. PATENT DOCUMENTS

| | | | |
|---|---|---|---|
| 5,150,080 A * | 9/1992 | Bianchini et al. | 331/99 |
| 6,359,444 B1 * | 3/2002 | Grimes | 324/633 |
| 6,997,039 B2 | 2/2006 | Rao et al. | |
| 7,360,461 B2 | 4/2008 | Desrochers et al. | |
| 7,538,400 B2 | 5/2009 | Segal et al. | |
| 8,281,642 B2 * | 10/2012 | Lee et al. | 73/31.01 |
| 2004/0016287 A1 | 1/2004 | Fu | |
| 2004/0113846 A1 * | 6/2004 | Achim | 343/700 MS |
| 2005/0116831 A1 | 6/2005 | Zribi | |
| 2005/0262943 A1 | 12/2005 | Claydon et al. | |
| 2007/0068493 A1 * | 3/2007 | Pavlovsky | 123/479 |
| 2009/0145233 A1 * | 6/2009 | Eklund et al. | 73/649 |
| 2010/0190270 A1 | 7/2010 | Piazza et al. | |

OTHER PUBLICATIONS

McGrath et al, Carbon Nanotube Based Microwave Resonator Gas Sensors, International Journal of High Speed Electronics and Systems, vol. 16, Issue 04, Dec. 2006.*

(Continued)

*Primary Examiner* — Hezron E Williams
*Assistant Examiner* — Alexander Mercado
(74) *Attorney, Agent, or Firm* — Dorsey & Whitney LLP

(57) ABSTRACT

Techniques are generally described for detecting a concentration level of at least one gas. Some example devices may include a sensor including conductive plate on a surface of dielectric including a nanotube layer formed thereon. The conductive plate and the nanotube layer form a resonator that resonates at a frequency in response to an interrogation signal. The nanotube layer may be configured to associate with one or more gas molecules. The frequency at which the resonator resonates may shift according to which gas molecules are associated with the nanotube layer to identify a particular gas. An amount of resonance may be exhibited as a resonant response signal. An amplitude of the resonant response signal may be indicative of the concentration level of the detected gas.

33 Claims, 10 Drawing Sheets

(56) References Cited

OTHER PUBLICATIONS

Abraham, J. K. et al., "A compact wireless gas sensor using a carbon nanotube/PMMA thin film chemiresistor", Smart Materials and Structures, Aug. 6, 2004, vol. 13, No. 5, pp. 1045-1049.

Bogue, R. W. et al., "Nanotechnology: what are the prospects for sensors?", Sensor Review, 2004, vol. 24, No. 3, pp. 253-260.

Cantalini, C., "Carbon nanotubes as new materials for gas sensing applications", Journal of the European Ceramic Society, 2004, vol. 24, No. 6, pp. 1405-1408.

Cantalini, C. et al., "NO2 gas sensitivity of carbon nanotubes obtained by plasma enhanced chemical vapor deposition", Sensors and Actuators B, 2003, vol. 93, pp. 333-337.

Chopra, S. et al., "Selective gas detection using a carbon nanotube sensor", Applied Physics Letters, Sep. 15, 2003, vol. 83, No. 11, pp. 2280-2282.

Lu, Y. et al., "A carbon nanotube sensor array for sensitive gas discrimination using principal component analysis", Journal of Electroanalytical Chemistry, Aug. 1, 2006, vol. 593, Issues 1-2, pp. 105-110.

Ong, K. G. et al., "A Wireless, Passive Carbon Nanotube-Based Gas Sensor", IEEE Sensors Journal, Apr. 2002, vol. 2, No. 2, pp. 82-88.

Penza, M. et al., "Carbon nanotubes as SAW chemical sensors materials", Sensors and Actuators B: Chemical, Jun. 1, 2004, vol. 100, No. 1-2, pp. 47-59.

Sivaramakrishnan, S. et al., "Carbon nanotube-coated surface acoustic wave sensor for carbon dioxide sensing", Sensors and Actuators B, 2008, vol. 132, pp. 296-304.

Tu, X. et al., "DNA Sequence Motifs for Structure Specific Recognition and Separation of Carbon Nanotubes", Nature Letters, Jul. 9, 2009, vol. 460, pp. 250-253.

Wang, Y. et al., "A Review of Carbon Nanotubes-Based Gas Sensors", Journal of Sensors, vol. 2009, pp. 1-24.

Zee, F. et al., "Micromachined polymer-based chemical gas sensor array", Sensors and Actuators B: Chemical, Jan. 25, 2001, vol. 72, Issue 2, pp. 120-128.

International Search Report and Written Opinion of the International Searching Authority dated Aug. 30, 2010 for Application No. PCT/US2010/041572.

* cited by examiner

GAS SENSOR USING NANOTUBES

BACKGROUND

Unless otherwise indicated herein, the materials described in this section are not prior art to the claims in this application and are not admitted to be prior art by inclusion in this section.

Many dangerous gases are not easily detected by human senses. For instance, Radon-222 gas is odorless, tasteless, and invisible and thus cannot be detected by human senses. As radon-222 decays, it emits alpha particles, which can damage lung tissue and has been linked to causing lunch cancer in humans. Air quality monitors have been used to detect such dangerous gases. Often, however, the design of these air quality monitors may limit the number of gases that may be detected so that many different monitors may be required to detect a wide variety of gases. Additionally, traditional air quality monitors are large and in some cases the accuracy of the monitors may depend on outside factors, such as humidity, temperature, and gas concentration level.

The present disclosure recognizes that it may be difficult and/or expensive to sense liquids with a vapor pressure sufficient to reach a detectable concentration in air. It may be difficult and/or expensive to sense vapors released by a sublimating solid. It may also be difficult to detect a chemical vapor deposition monolayer thickness and/or corresponding gas phase concentration.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

In the drawings.

SUMMARY

Figure 1A:
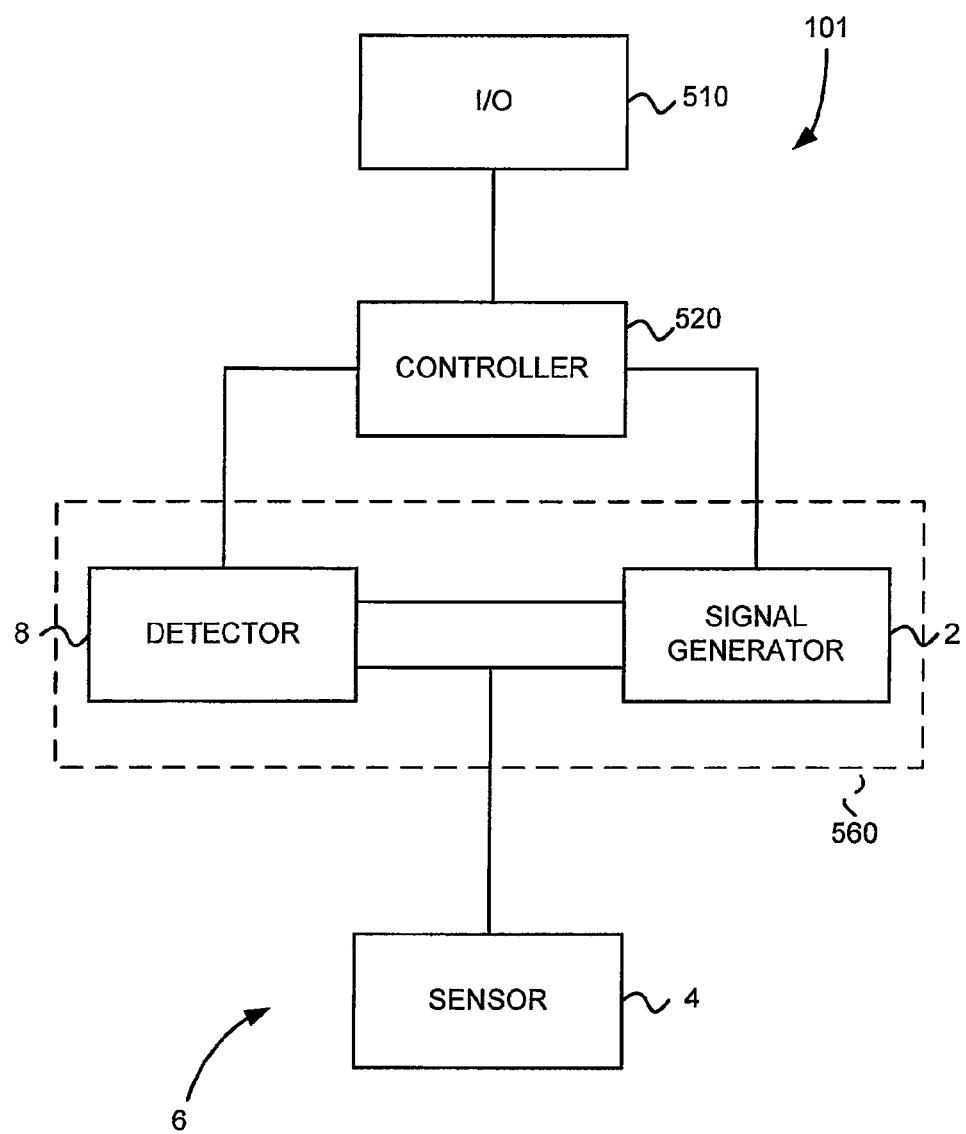
FIG. 1A is a block diagram of a system configured to identify at least one gas in a mixture of gases.

The present disclosure generally describes sensors configured to detect at least one gas in a volume that includes a mixture of two or more gases. Some example sensors may include a dielectric substrate, a conductive plate on a first surface of the dielectric substrate, and a nanotube layer arranged on the conductive plate. The conductive plate, in combination with the nanotube layer, may form a resonator. The resonator may be configured to generate a resonant response signal in response to an interrogation signal. The resonant response signal may be indicative of a resonance characteristic of the resonator that changes when the sensor is in contact with the at least one gas in the volume, such that the resonance characteristic of the resonator identifies the at least one gas.

The present disclosure also generally describes systems for detecting at least one gas in a volume that includes a mixture of two or more gases. Some example systems may include a signal generator, at least one sensor, and a detector. The signal generator may be configured to provide an interrogation signal. The at least one sensor may include a resonator and may be configured to receive the interrogation signal and to generate a resonant response signal in response to the interrogation signal. The resonant response signal may be indicative of a resonance characteristic of the resonator that changes when the at least one sensor is in contact with the at least one gas in the volume, such that the resonance characteristic of the resonator identifies the at least one gas. The detector may be configured to receive the resonant response signal and generate a detection signal that indicates the resonance characteristic of the resonator that identifies the at least one gas.

The present disclosure further describes methods for identifying two or more gases in a volume including a mixture of two or more gases. Some sample methods include applying one or more interrogation signals to a resonator, measuring two or more resonant responses of the resonator when excited by interrogation signals, and determining the identity of two or more gases as a function of the two or more resonant responses. In some examples methods, the resonator includes carbon nanotubes.

The present disclosure also generally describes methods for identifying a gas in a mixture including two or more gases. Some example methods include receiving a radio based interrogation signal with an antenna. The radio based interrogation signals may include a plurality of interrogation frequencies. The antenna may be is operatively coupled to a carbon nanotube resonator or formed at least in part by the carbon nanotube resonator. Some example methods may further include generating at least one resonant response in response to the radio based interrogation signal with the carbon nanotube resonator and identifying the gas in contact with the carbon nanotube resonator based on the at least one resonant response. In some example methods, the resonant response of the carbon nanotube resonator varies based on content of the gas mixture that are in contact with the carbon nanotube resonator.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

The following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are implicitly contemplated herein.

This disclosure is drawn, inter alia, to methods, systems, devices, and/or apparatuses generally related to detecting a presence and/or concentration level of at least one gas. Some example devices may include a sensor including a dielectric substrate, a conductive plate, and a nanotube layer on the conductive plate. The conductive plate may be provided on a first surface of the dielectric substrate. The nanotube layer may be arranged on the conductive plate such that the nanotube layer and the conductive plate form a resonator that electromagnetically resonates at a frequency in response to an electromagnetic interrogation signal. The nanotube layer may be configured to associate with one or more gas molecules. For instance, the nanotube layer may be configured to adsorb gas molecules. The frequency at which the resonator resonates may shift according to which gas molecules are associated with the nanotube layer. Resonance may be exhibited as a resonant response signal. An amplitude of the resonant response signal may be indicative of the presence and/or concentration level of the detected gas. A resonant frequency may further be detected as frequency corresponding to a phase inversion of the resonant response signal.

The resonator has a base resonant frequency. In response to the nanotube layer associating with one or more types of gas molecules, the resonant frequency of the resonator may shift to a second or shifted resonant frequency, indicating a gas in contact with the sensor. More particularly, each type of gas molecule that is associated with the nanotube layer may produce a particular characteristic resonant frequency shift in the resonator. That is, the magnitude of the frequency shift may be indicative of a species of gas detected. Thus, in some examples, a single resonator may be configured to detect a wide variety of gases to which the sensor may be exposed.

FIG. 1A is a block diagram of a system 1 configured to identify at least one gas in a mixture of gases, according to at least some embodiments described herein. A signal generator 2 may be configured to generate at least one electromagnetic interrogation signal (or simply an interrogation signal), where each interrogation signal includes one or more associated frequencies (e.g., a broadband signal with a range of frequencies, or a narrowband signal with a reduced range of frequencies). Optionally, the signal generator 2 may be configured to generate a plurality of electromagnetic interrogation signals. The signal generator 2 is operatively coupled to at least one sensor 4, where sensor 4 can be disposed in a volume 6 including a mixture of gases. The sensor 4 can be configured to receive the at least one interrogation signal generated by the signal generator 2, resulting in excitation of the sensor such that the sensor may provide a resonant response signal while excited. The resonant response signal includes a resonant frequency indicative of the presence of the at least one gas in the mixture of gases in the volume 6. Optionally, the sensor 4 may be configured to receive a plurality of electromagnetic interrogation signals from the signal generator 2, resulting in excitation of the sensor such that the sensor may provide a resonant response signal including two or more resonant frequencies, each of the two or more resonant frequencies being determined by a respective gas contacting the sensor 4. A detector 8 can be configured to evaluate the resonant response of the at least one sensor 4. The detector 8 may be operated to detect the resonance characteristics (e.g., resonant frequency, shift in resonant frequency, Q of the resonance, etc.) of sensor 4, which is indicative of the presence of the at least one gas about sensor 4. Optionally, the detector 8 may be configured to detect two or more resonant frequencies associated with sensor 4 to identify the two or more gases in the mixture of gases about sensor 4.

Figures 1B, 1C:
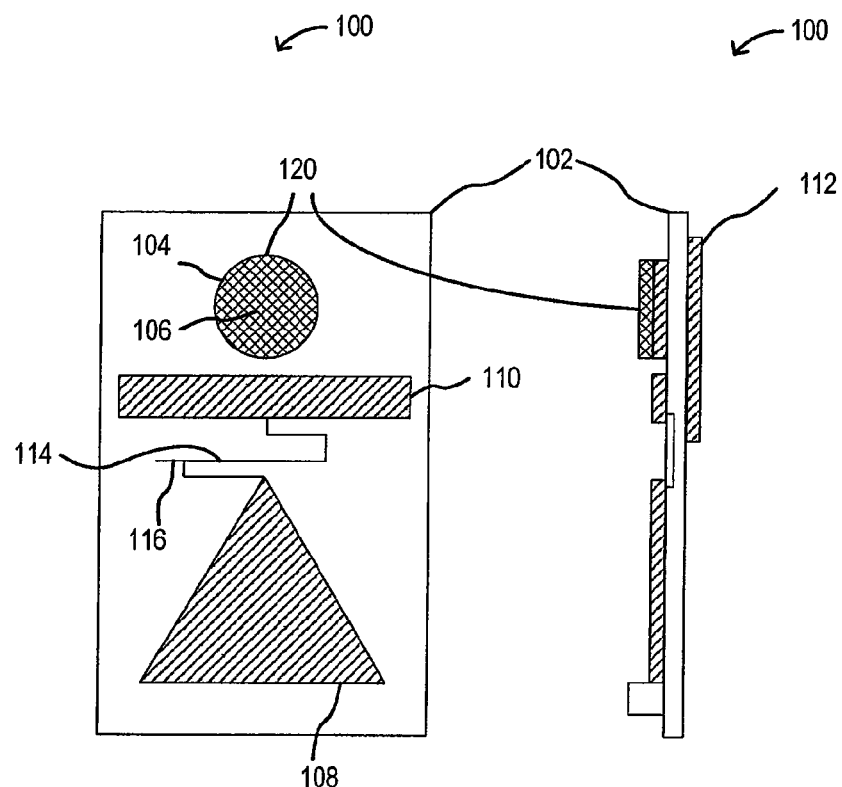
FIG. 1B is a depiction of some example sensors for detecting one or more gases.
FIG. 1C is a depiction of a side view of the example sensor of FIG. 1B.

FIGS. 1B and 1C are depictions of some example sensors 100 configured to detect one or more gases are shown in accordance with at least some examples of the present disclosure. The example sensor 100 can be substituted for the sensor 4 in the system 101 of FIG. 1A. As illustrated in FIGS. 1B and 1C, the example sensor 100 further includes a conductive plate 104. According to some embodiments, the conductive plate 104 may be formed as an etched copper layer. A layer of carbon nanotubes 106 is supported by the conductive plate 104. According to some embodiments, the layer of carbon nanotubes 106 may either include and/or consist essentially of single wall carbon nanotubes. According to some non-limiting embodiments, the carbon nanotubes may be formed as a self-assembled monolayer (SAM) on the conductive plate.

The layer of carbon nanotubes 106 may be arranged to contact the mixture of gases in the volume 6. The conductive plate 104 and the layer of carbon nanotubes 106 are configured to cooperate to form a resonator 120. Resonator 120 has a characteristic resonant frequency when excited by an interrogation signal. The characteristic resonant frequency of the resonator 120 can be referred to as a base resonant frequency when the resonator is in a default condition such as in a vacuum. While the base resonant frequency may typically refer to the first harmonic response of the excited resonator 120, some embodiments may use a second or higher harmonic or a subharmonic to the first harmonic as the base resonant frequency. Similarly, shifted resonant frequencies (described more fully below) may refer to harmonics or subharmonics of a first harmonic response. Harmonics and/or subharmonic systems may use suitable filtering and/or tuning of detector 8 components, and/or parasitic resistance and/or capacitance of circuitry of the system 101, for example.

When the resonator 120 is exposed to an environment that is different from the default condition (i.e., not in a vacuum, and therefore in the presence of a gaseous environment), the characteristic resonant frequency of the resonator 120 exhibits a shifted resonant frequency. The amount of shift in the resonant frequency of resonator 120 is determined, at least in part, by the presence of the at least one gas. According to one view, the shifted resonant frequency is determined by a change in conductivity of the carbon nanotubes responsive to adsorption of molecules of the at least one gas. According to another view, the valence of an adsorbed molecule interacts with the conduction band of a carbon nanotube to change the electron mobility of the carbon nanotube. The aggregate change(s) in electron mobility changes the resonant response(s) of the resonator 120.

The breadth of a resonant response may be narrowed (for example as half-max bandwidth) to improve response specificity. One way to reduce the range of frequencies present in a resonant response may be to use carbon nanotubes that are size classified, for example using polypeptide or polynucleotide sorting methods. This may be used to produce a layer of carbon nanotubes 106 that are substantially all about the same size. The narrow size distribution of the carbon nanotubes may produce a higher Q-factor in the resonator 120, which narrows the range of resonant frequencies corresponding to a single resonant peak. A resonator 120 having a higher Q-factor also exhibits the additional effect of increasing relative response amplitude. The resonant response amplitude is, at least in part, proportional to the concentration of a particular gas corresponding to the resonant frequency. Hence, increasing Q-factor may also improve system 101 sensitivity and reduce the minimum concentration at which a gas may be detected.

Another way to reduce the range of frequencies present in a resonant response is to reduce wavelength diversification related to polarization-dependency of frequency. For example, the conductive plate 104 may be circular. Deviations from circularity may be minimized to increase the Q-factor. According to some embodiments, a high aspect ratio rectangle or other polygon (e.g., greater than 10:1 size ratio) may be utilized for conductive plate 104 such that conductive plate 104 may provide a bi-modal resonant response that can be filtered.

The sensor 100 may include at least one feedline 110 operatively coupled to the signal generator 2 and the detector 8. The feedline 110 may be configured to receive at least one interrogation signal from the signal generator 2, and excite the resonator 120 with the interrogation signal. If the at least one resonator 120 exhibits resonance at a frequency associated with the interrogation signal (i.e., if a corresponding gas is present), the feedline 110 may also receive the resonant response signal from the at least one resonator 120 and conduct the resonance response signal to the operatively coupled detector 8.

In the example of FIGS. 1A and 1B, the sensor 100 may be formed on a dielectric substrate 102. A ground plane 112 may also be formed on the dielectric substrate 102. The ground plane is typically separate from (i.e. insulated from) the resonator 120 and the feedline 110 to close a resonant circuit between the feedline 110 and the resonator 120. In this way, the resonator 120 and the ground plane 112 may effectively form a patch antenna that has tuned response determined by gases present in the environment. In some embodiments, the resonator 120 and ground plane 112 may be directly interrogated by a radio signal. In the embodiments shown in FIGS. 1A and 1B, the at least one feedline 110 is operatively coupled to one or more of the signal generator 2 and the detector 8 via a radio interface including an antenna 108.

Figure 2:
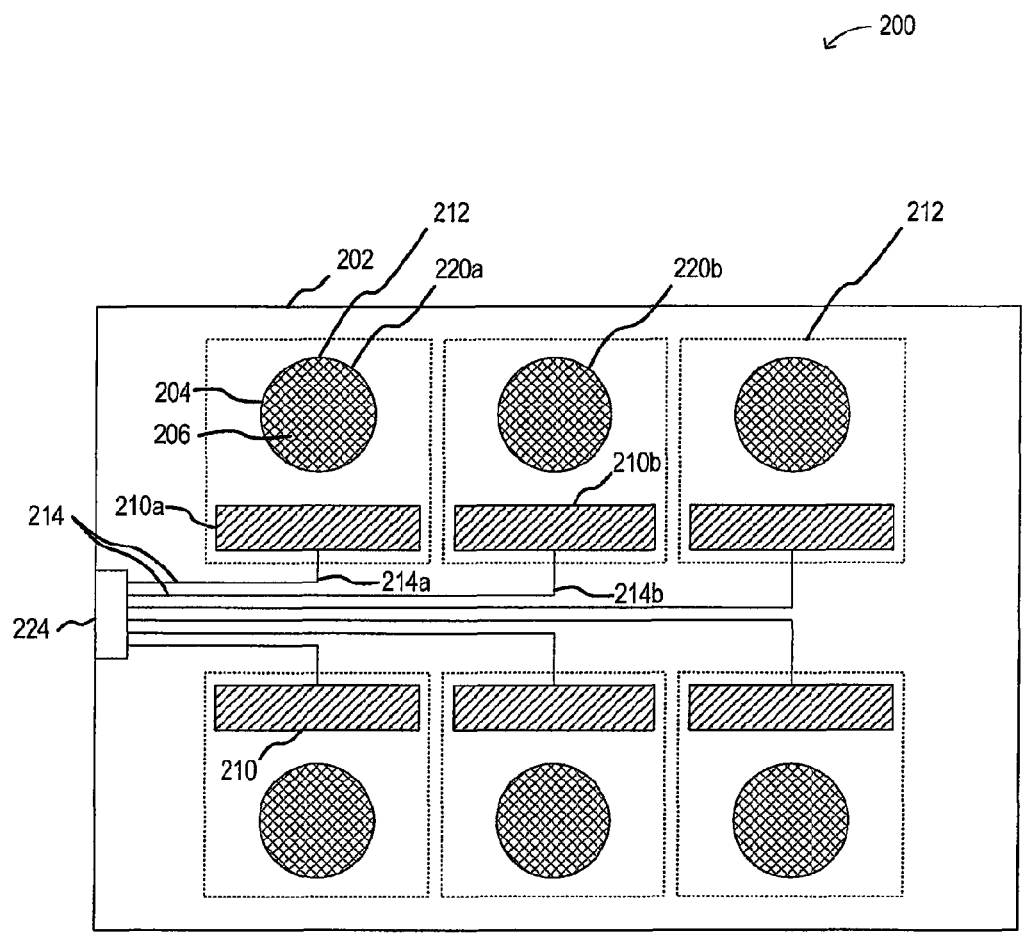
FIG. 2 is a depiction of some example sensors for detecting one or more gases.

FIG. 2 is a depiction of some example sensors 200 for detecting one or more gases, in accordance with at least some examples described herein. The example sensor 200 can be substituted for the sensor 4 in the system 101 of FIG. 1A. As illustrated, an example sensor 200 may include a plurality of feedlines 210a, 210b that are electrically isolated from one another. The sensor 200 may include a corresponding plurality of resonators 220a, 220b operatively coupled to the feedlines 210a, 210b. In such an example, sensor 200 may include a switch 224 that is configured to selectively couple the signal generator 2 and the detector 8 to the plurality of feedlines 210a, 210b, such as via respective traces 214a, 214b.

The plurality of resonators 220a, 220b may each be configured to resonate at the at least one frequency output by the signal generator 2 responsive to a presence of a particular gas in the mixture of gases. Each of the plurality of resonators 220a, 220b may have different sizes with respect to one another, such that each of the resonators is responsive to the presence of a different gas. The response of a particular resonator 220a, 220b may be measured by aligning the switch 224 to couple the feedline 210a, 210b corresponding to the particular resonator 220a, 220b to the signal generator 2 and detector 8 (FIG. 1A). By selecting a base resonant frequency for each resonator, the shifted resonance frequency for a particular gas may be tuned to respond to a particular frequency associated with a selected interrogation signal. According to some embodiments, the signal generator 2 and detector 8 may be configured to respectively generate and detect substantially one frequency, but the system 101 may still be configured to detect a plurality of gases by selecting the different feedlines 210a, 210b and resonators 220a, 220b.

Figure 3:
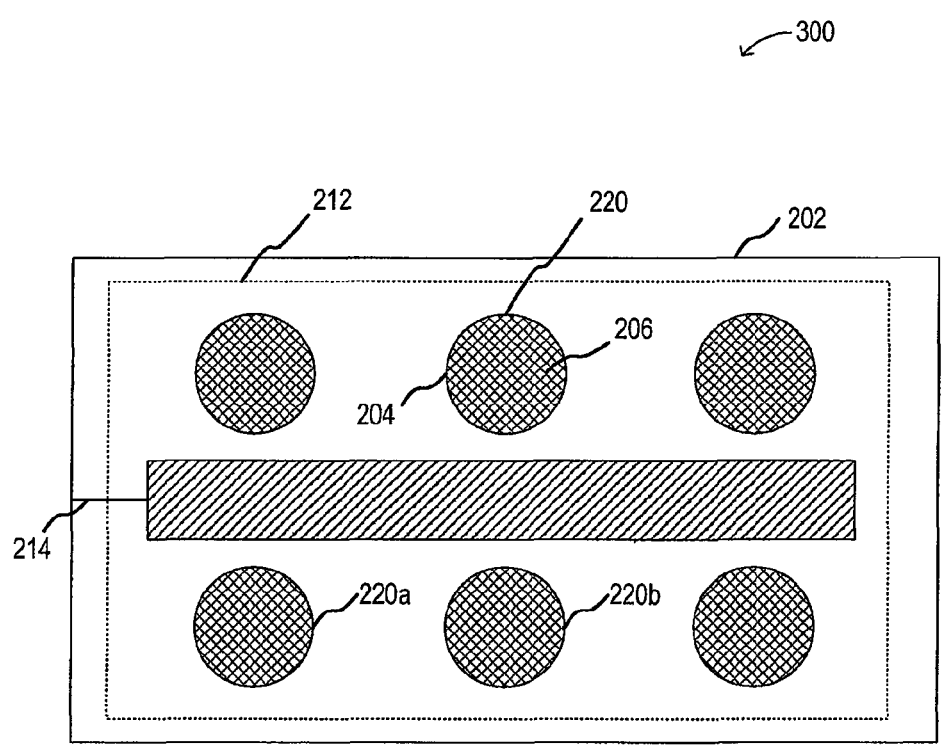
FIG. 3 is a depiction of some example sensors for detecting one or more gases.

FIG. 3 is a depiction of some example sensors 300 for detecting one or more gases in accordance with at least some examples described herein. The example sensor 300 can be substituted for the sensor 4 in the system 101 of FIG. 1A. A sensor 300 is depicted that includes a plurality of resonators 220a, 220b operatively coupled to one feedline 210. Each of the plurality of resonators may be different sizes. That is, the plurality of resonators 220a, 220b may each be configured to resonate at a different shifted resonant frequency responsive to a presence of a different respective gas in the mixture of gases. For example, the example sensor 300 may be utilized in the example system 101 of FIG. 1, which may include a signal generator 2 configured to generate one or more interrogation signals with a plurality of associated frequencies corresponding to the respective different shifted resonant frequencies. The detector 8 in the example system 101 can be configured to detect the shifted resonant frequencies by evaluating the resonant response signals when the resonators are excited by the interrogation signal. In this way, the system 101 (e.g., see FIG. 1A) may operate at frequencies of interrogation and response signals that are distributed across the spectrum differently than the distribution of frequency shifts, because each characteristic shift is from a selected base frequency.

Referring again to FIG. 1A, the detector 8 may be configured to output a signal (i.e., a detection signal) associated with the detection of the at least one gas. The detection signal may be either an analog signal (e.g., voltages, currents, etc) or a digital signal (e.g., data bits). A controller 520 may be operatively coupled to the detector 8 and receive the detection signal. The controller 520 may be configured to determine the presence of the at least one gas responsive to receiving the detection signal from the detector 6. A data interface 510 may also be operatively coupled to the controller 520. In some embodiments, the controller 520 can be configured to assert an alarm condition when the presence of the at least one gas is determined from the received detection signal. For example, the controller 520 may be configured to assert an alarm via data interface 510 to output a human-detectable signal responsive to the detected presence of the at least one gas.

The volume 6 may be an air volume at atmospheric pressure. In some embodiments, the volume 6 may be an air volume and the at least one gas that is detected may be radon.

Figure 5:
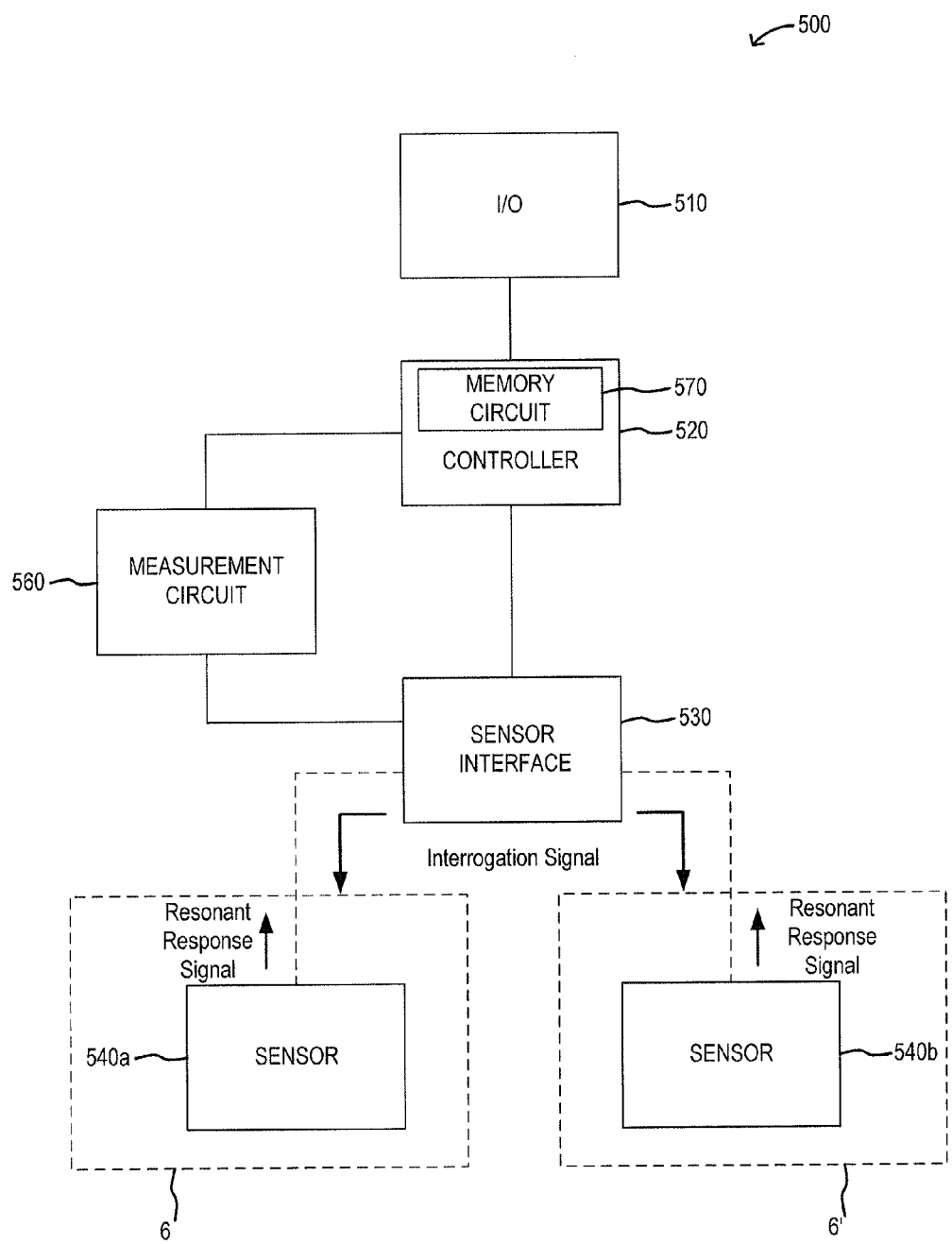
FIG. 5 is a block diagram of some example sensor systems for determining a concentration level of one or more gases.

Referring to FIG. 5, the at least one sensor may include two sensors 540a, 540b disposed in respective different air volumes. A measurement circuit 560 including the signal generator and detector may be operatively coupled to the two sensors 540a, 540b. Respective resonant response signals may be received from the two sensors 540a, 540b. The measurement circuit 560 may be configured to detect the presence of the at least one gas in one of the air volumes by comparing respective resonant response signals received from the two sensors 540a, 540b.

Referring again to FIGS. 1B and 1C are depictions of some example sensors 100 configured to detect one or more gases are shown in accordance with at least some examples of the present disclosure. FIG. 1B is a top view of the example sensor 100 and FIG. 1C is a side view of the example sensor 100. The example sensor 100 may include a dielectric substrate 102, a conductive plate 104, a nanotube layer 106 disposed on the conductive plate 104, and a feedline 110 configured to apply an interrogation signal to the resonator 120. A groundplane 112 may be formed on the back of the dielectric substrate 102, or alternatively may be formed from a conductive housing or other material in proximity to the resonator 120 and the feedline to electromagnetically couple the resonator 120 and the feedline 110.

The sensor 100 may optionally include an interrogation antenna 108 operatively coupled to the feedline 110 via a trace 114 with a detuning stub 116. The dielectric substrate 102 is an insulating material. In one example, the dielectric material may be an FR-4 grade material as designated by the National Electrical Manufacturing Association. The conductive plate 104 may be disposed on a first surface of the dielectric substrate 102. The conductive plate 104 may be physically attached to the dielectric substrate 102 using a variety of means such as, for example, a bonding agent or adhesive layer, a eutectic type of attachment, a solder type of attachment, or another coupling means. In some examples, the conductive plate 104 may be formed on the surface of the dielectric substrate 102 using a electro-plating solution, etching, sputtering, etc. In some examples, the conductive plate 104 may be a copper conductive plate. In some examples, the conductive plate 104 and the feedline 110 (and optionally other components, such as the interrogation antenna 108, trace 114, detuning stub 116, and ground plane 112 shown in FIG. 1B) are formed by masking and etching a conductor layer provided by a circuit board vendor.

The nanotube layer 106 may be a layer of nanotubes arranged on a surface of the conductive plate 104 to form a resonator 120. In some examples, the nanotube layer 106 may comprise a plurality of carbon nanotubes and may be deposited onto the conductive plate 104 using an appropriate method, such as a vapor based deposition method. In another example, the nanotube layer 106 may be formed by coating, dipping, spraying, spin coating, or screen printing a solution including nanotubes. The nanotubes may be deposited onto a curable binder, or the solution may include a curable binder. In some examples, the layer of nanotubes may be comprised of a monolayer.

The feedline 110 may be disposed on the first surface of the dielectric substrate 102. The groundplane 112 may be disposed on an opposite side of the dielectric substrate 102 than the feedline 110 and the conductive plate 104. In some examples, the groundplane 112 may have a footprint that is larger than the feedline 110 and the conductive plate 104 and be positioned to extend beyond the feedline 110 and the conductive plate 104. The feedline 110 may be physically connected to a frequency source, or the feedline may be operatively coupled to a frequency source via radio frequency interrogation through an interrogation antenna 108. The interrogation antenna 108 may be coupled to the feedline 110 by the trace 114. The interrogation antenna 108 may be configured to receive an interrogation signal that corresponds to a swept range of interrogation frequencies and provide the swept interrogation frequencies to the feedline 110. The feedline 110 may provide the interrogation signal to the resonator 120. When the interrogation signal from the feedline 110 has a frequency that corresponds to the resonance frequency of the resonator 120, the resonator 120 may resonate. That is, the resonator 120 resonates in response to the interrogation signal. The detuning stub 116 may be operatively coupled to the interrogation antenna 108 or the trace 104. The detuning stub 116 reduces the quality factor (Q factor) of the antenna and feedline to allow transmission of a broader range of interrogation frequencies to the resonator 120.

The interrogation signal may include a specified fundamental frequency for the resonator. In other examples, the interrogation signal may include one or more harmonics or sub-harmonics of the fundamental frequency. The resonance of the resonator 120 causes a resonant response signal to be generated, which may be exhibited as reflectivity in the feedline 110. For instance, the resonance frequency of the resonator 120 may be sensed by a change in resonant response of the interrogation signal.

As discussed above, the nanotube layer 106 may associate with one or more gas molecules. In some examples, the nanotube layer 106 may associate with the one or more gas molecules by adsorbing the one or more gas molecules into an opening in the nanotube(s), onto a surface of the nanotube(s), in the interstitial space between adjacent nanotubes, or a combination thereof. A resonance frequency associated with the resonator 120 may shift according to which gas molecules are associated with the nanotube layer 106. In particular, the resonator 120 may have a first characteristic resonant frequency. In response to the nanotube layer 106 associating with a type of gas molecule, a portion of the resonant response of the resonator 120 to electromagnetic interrogation shifts from the base resonant frequency to a first shifted resonant frequency. As described above, the resonance may be detected in the feedline 110 as a resonant response of the interrogation signal at a characteristic frequency (or a shifted characteristic frequency). Similarly, in response to the nanotube layer 106 associating with another type of gas molecule, a portion of the resonant response of the resonator 120 shifts to a second shifted resonant frequency.

In some examples, the sensor 100 may be used in air, and the base resonant response of the resonator 120 includes frequency components corresponding to vacuum, nitrogen, oxygen, argon, and carbon dioxide responses. Changes in concentration level of the components of air results in corresponding changes in amplitude of the resonant responses. Addition of another gas results in some of the resonant response corresponding to the component of air being shifted to another shifted response frequency corresponding to the added gas. In another example, the sensor 100 may be operated in a base environment consisting essentially of a single pure gas such as argon or another gas selected not to mask a response. A test gas may be injected into the space surrounding the resonator 120, and the resonant shift may be measured as a change from the resonant behavior in the system in the single pure base gas.

The sensor 100 may include an integrated measurement circuit (not shown) that is configured to provide interrogation frequencies and measure an amplitude and/or frequency of the resonant response signal. In other examples, the measurement circuit may be external to the sensor 100. In other embodiments, the sensor 100 may include a radio interface (not shown) including an antenna and a transceiver. In such embodiments, all or portions of the apparatus of FIG. 1A may be integrated onto the substrate 102.

The resonant response signal that is measured by the measurement circuit (not shown, whether integrated into the sensor 100 or separate) may be used to determine a concentration level of the detected gas. In particular, the amplitude of the shifted resonance frequency may be a function of the concentration level of the detected gas. Thus, the change in amplitude may indicate a concentration level associated with a detected gas in the surrounding air in which the sensor 100 is located. The resonator 120 may also be configured to detect a plurality of gases by resonating at corresponding plurality of shifted resonant frequencies, where the magnitudes of the resonant frequency shifts are indicative of the particular gases present, and the amplitudes at the shifted frequencies is indicative of the respective concentration levels of the corresponding gases. The amount of a frequency shift (e.g., change in Hertz) at which the resonance occurs may be a function of the species of gas detected.

In some examples, rather than including the interrogation antenna 108, the sensor 100 may include another type of frequency source, such as an oscillator. In some alternative examples, the sensor 100 may be operatively coupled to an external frequency source via a connector.

Referring again to FIG. 2 is a depiction of some example sensors 200 for detecting one or more gases in accordance with at least some examples of the present disclosure. The sensor 200 includes a dielectric substrate 202 including a plurality of resonators 220a, 220b, etc., each resonator 220 including a conductive plate 204 with a nanotube layer 206 formed thereon. The sensor 200 may further include a plurality of feedlines 210a, 210b, etc, traces 214a, 214b, etc, and groundplanes 212. Each trace 214 may be operatively coupled to a frequency source (not shown), such as a single or multi-frequency interrogation antenna (not shown), on or external to sensor 200. If the frequency source is external to sensor 220, the frequency source may be operatively coupled to the traces via an external connector. Each resonator 220 may be operatively coupled to a respective feedline 210. Each groundplane 112 may be formed on an opposite side of the dielectric substrate 202 than the resonators 220 and overlap a corresponding feedline 210 and resonator 220. The frequency source may be configured to selectively provide an interrogation signal to each feedline 210 via each respectively operatively coupled trace 214. In particular, the sensor 200 or an external device may include a switch 224 operatively coupled to the frequency source and each feedline 210 configured to selectively couple the frequency source to the respective feedline 210. Each feedline 210 may be configured to apply the interrogation signal with associated frequency to a corresponding resonator 220.

Each resonator may have a measured or designed base resonant frequency and may be configured to exhibit a shifted resonance in response to one or more gases associating with its nanotubes. In some examples, each resonator 220 may be configured to resonate at a shifted resonance in response to the same interrogation signal and in response to different gases associating with the nanotubes 206 on the respective resonator 220. In particular, a shifted resonance frequency of each resonator 220 may be selected based on the diameter of the conductive plate 204.

Resonance frequency of a resonator 220 in a vacuum may be determined according to the following relationship:

$$fo = (1.841 \times c)/(2 \times n \times r \times \sqrt{\xi})$$

where
fo is the resonant frequency of the resonator;
c is the speed of light
r is the radius of the disk;
n is a whole number where 1 is the fundamental frequency, 2 is the second harmonic, etc.; and
$\sqrt{\xi}$ is the square root of the relative dielectric constant of the substrate.

That is, each resonator 220 may be configured to resonate at a particular frequency for a particular gas based on the diameter of the resonator 220. For example, by having a plurality of resonators 220 each having varying diameters, the resonance shift in frequency at which each resonator resonates when a particular gas associates with the nanotube layer 206 on the resonator 220 may be predetermined. By varying the diameter of the conductive plate, this will allow each resonator 220 to be configured to resonate in response to a particular frequency. Thus, the base frequency of each resonator 220 may be back calculated as a negative of a shifted resonance that corresponds to a particular gas and a particular diameter of a conductive plate. In some examples, each resonator 220 may be configured to resonate in response to an interrogation signal having a frequency within a band that does not require an FCC license in which to operate. For instance, the swept range of interrogation frequencies received by the interrogation antenna may be in an unlicensed band.

In some examples, the switch 224 may be configured to selectively couple a first feedline 214a to an output of the frequency source to apply an interrogation signal with a first frequency $f_1$ to a first resonator 220a. The first resonator 220a may be configured to resonate in response to nanotubes 206 that are associated with a first gas, such as Radon, and in response to the interrogation signal. The switch 224 may be configured to decouple the first feedline 214a from the frequency source and couple a second feedline 214b to the frequency source. A second resonator 220b operatively coupled to the second feedline 214b may be configured to resonate in response to its corresponding nanotube layer 206 associating with a second gas, such as $CO_2$ and in response to the interrogation signal with frequency $f_1$.

The switch 224 may be configured to switch between coupling and decoupling each trace 214 to provide the interrogation signal $f_1$ to each resonator 220 one at a time. The switching between the coupling and decoupling may be provided either sequentially (i.e., each trace is switched in or out in a sequential order) or non-sequentially (i.e., traces selectively switched in or out in a non-sequential order). In some examples, the interrogation signal that is switched in and out between the different traces 214 may be the same as the other. Therefore, in these examples, the frequency source may be a single frequency oscillator. However, in other examples, the interrogation signals that excite each resonator 220 may differ from one another.

As indicated above, a diameter of each conductive plate 204 of the resonator 220 may be adjusted to set the frequency at which the resonator 220 resonates in response to nanotubes 206 formed thereon associating with a particular gas. For instance, a first resonator 220 may be designed with a particular diameter to resonate in response to radon gas associating with its nanotubes 206 formed thereon and in response to an interrogation signal with a particular frequency $f_1$ (or a band of frequencies substantially centered at the particular frequency). A second resonator 220 may be designed with a particular diameter to resonate in response to $CO_2$ gas associating with its nanotubes 206 formed thereon and in response to the same interrogation signal with the same particular frequency $f_1$. Therefore, the same interrogation signal may be applied to each of the resonators 220 through the feedlines 214. Although the second resonator 220b may also resonate in response to nanotubes 206 being associated with the first gas, radon, the resonant frequency may be outside of the range of frequencies (or frequency band) of the interrogation signal, and the second resonator 220b will therefore not provide a response corresponding to radon, but rather will provide a response corresponding to a different selected gas.

As indicated above, when each resonator 220 resonates, a resonant response signal is exhibited as electromagnetic reflectivity in the feedline 210. The amplitude of the resonant response signal may be measured to determine a concentration level of a gas detected by a particular resonator 220. The resonant response signal may be provided to a controller located on the sensor 200 or externally coupled to the sensor 200. The controller may access the LUT discussed below to identify the gas detected based on which resonator 220 resonated and to determine the concentration level of the gas based on the amplitude of a particular resonant response signal. The sensor may configured to be wired or wirelessly coupled to the controller.

FIG. 3 is a depiction of some example sensors 300 for detecting one or more gases in accordance with at least some examples of the present disclosure. The example sensor 300 is similar to the example sensor 200 of FIG. 2. However, the example sensor 300 in FIG. 3 has a single feedline 210, trace 214, and groundplane 212. As in the sensor 200 of FIG. 2, the sensor 300 further includes a plurality of resonators 220 formed on a first surface of a dielectric substrate, each of the plurality of resonators 220 including a conductive disk 204 having a layer of nanotubes 206 formed thereon. The groundplane 212 may be formed on a surface opposite the plurality of resonators 220 and positioned to overlay the plurality of resonators 220 and the feedline 210.

A first end of the trace 214 may be operatively coupled to a frequency source (not shown), such as a single or multi-frequency interrogation antenna. The frequency source may be either located on the sensor 300 or external from the sensor 300. The other end of the trace 214 may be operatively coupled to the feedline 210. The feedline 210 may be configured to provide an interrogation signal to each of the plurality of resonators 220. In this example, the frequency source may be a multi-frequency interrogator configured to provide an interrogation signal to each resonator.

As in the sensor 200 of FIG. 2, each resonator 220 on the sensor 300 may have a base resonant frequency and may be configured to exhibit a shifted resonance frequency in response to gas associating with its nanotubes 206. In particular, each resonator 220 may be configured to shift its resonance in response to a particular gas being associated with its nanotubes 206 and in response to a particular frequency of the interrogation signal. For instance, the frequency source may provide a first interrogation signal with a first frequency $f_1$ to all of the plurality of resonators 220 via the feedline 210. A first resonator 220a may be configured to resonate in response to the first interrogation signal at the first frequency $f_1$.

The remaining resonators 220 may not respond to the first interrogation signal because the remaining resonators 220 may be designed to respond to different interrogation frequencies. For instance, a second resonator 220b may be configured to resonate in response to a second interrogation with a second frequency $f_2$. In some examples, the first frequency $f_1$ is different from the second frequency $f_2$. The first resonator and second resonators 220a and 220b may be configured to resonate in response to interrogation signals at different frequencies, $f_1$ and $f_2$, respectively, by changing the diameter of the conductive plate 214 on each respective resonator 220a and 220b. Therefore, each resonator 220 in the sensor 300 may be configured to resonate at a different frequency and in response to a different gas associating with each resonator's 220 nanotubes 206. In some examples, the interrogation frequencies may be selected from a narrow bandwidth, such as within a band that does not require an FCC license in which to operate.

When the first resonator 220a resonates, a resonant response signal may be exhibited in the feedline 210 in response to the first resonator 220a resonating, and the resonant response signal may be provided to a controller operatively coupled to or provided on the sensor 300. When a resonance is detected in response to a particular frequency of an interrogation signal, the controller may be programmed to detect which of the resonators 220 is resonating based on the frequency of the interrogation signal. That is, because each resonator 220 predominately resonates at a particular frequency (e.g., a specified fundamental frequency for the resonator, ignoring harmonics and sub-harmonics), when a resonator 220 resonates in response to an interrogation signal with the particular frequency, it is known which resonator 220 is resonating based on the interrogation signal's frequency that caused the resonance.

The geometry of the nanotube layer and/or the conductive plate in any of the example sensors 100-300 may vary depending on the type of gas sought to be detected. Additionally, a diameter of the nanotubes and/or a length of the nanotubes may vary depending on the gas to be detected. For example, a diameter of the nanotube may be similar to the size of a molecule of a gas to be detected. In another example, each of the nanotubes in the layer of nanotubes may have substantially the same diameter and length. In another example, each of the nanotubes on a conductive plate may have substantially the same diameter and be different in length from other nanotubes, or may be substantially the same length as other nanotubes and have different diameters.

Recent techniques have been developed that separate nanotubes according to length. For instance, one technique is described in Tu, X. et al., *DNA sequence motifs for structure-specific recognition and separation of carbon nanotubes*, Nature, 460, 250-253 (2009), which is incorporated by reference herein for all purposes and to the extent it is consistent with disclosure herein. By having nanotubes with substantially the same diameter and length, a quality factor (Q factor) of the resonator may be increased. Generally, decreased Q corresponds to reduced peak resonant amplitude that is distributed across a wider range of frequencies. Generally, increased Q corresponds to a reduced frequency range of resonant behavior and an increased peak resonant amplitude. By increasing the Q factor, a resonator may produce substantially distinct resonant shifts for different gases that have different but closely related resonant frequency shifts. In an example sensor, the diameter of the nanotubes may be on the order of a few nanometers and the length of the nanotube may be several millimeters in length. In some examples, the diameter of the nanotubes is slightly bigger than the gas or molecule that is being tested.

As is indicated above, in one example the gas being detected may be radon. Radon, such as Radon-222, is a radioactive gas, which is a naturally occurring element found, in varying amounts, in rock and soil. In this example, the nanotube may have a diameter comparable to the diameter of a radon gas molecule. In other examples, the gas being detected may be mercury fumes, lead fumes, benzene vapors, one or more gases indicative of a bomb, or any combination thereof. In examples, the mixture of gases may include air, such as nitrogen, oxygen, argon, and carbon dioxide at atmospheric pressure.

Figure 4A:
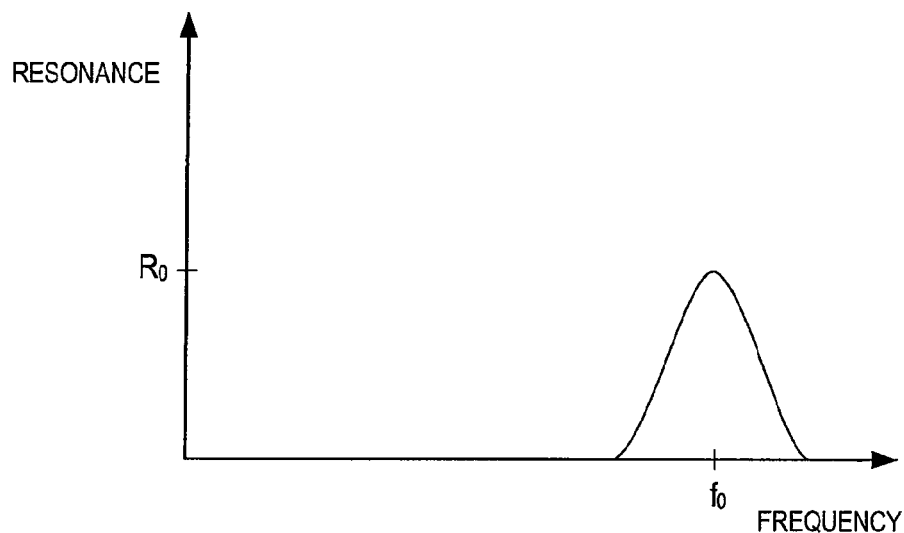
FIG. 4A is an illustrative graph of a base resonant response of an example resonator.
Figure 4B:
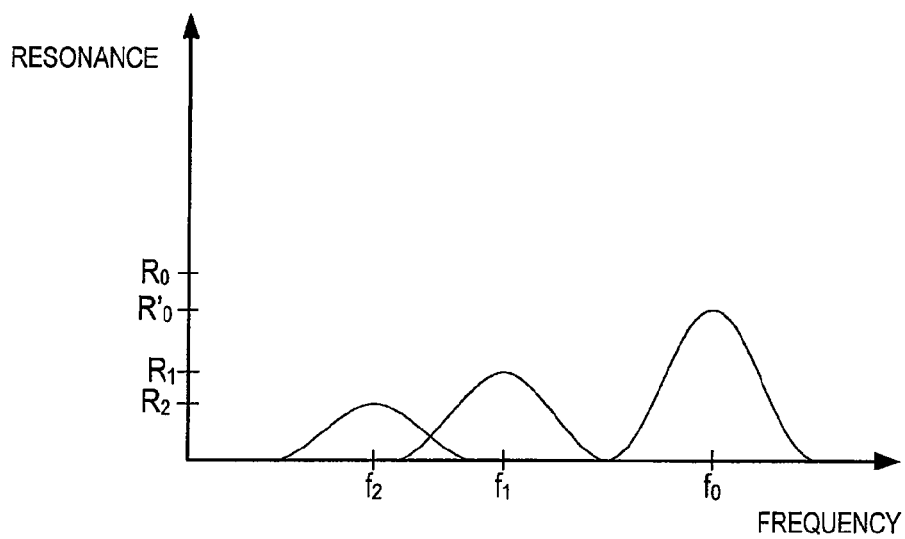
FIG. 4B is an illustrative graph of a shifted resonant response of an example resonator whose base resonant response is depicted in FIG. 4A.

The conductive plate may be made of a conductive material, for example metal, conductive polymer, semiconductor, polysilicon, etc. In some examples, the conductive plate includes a copper plate. In various examples, the nanotubes may be carbon nanotubes that are created by any appropriate method, such by one of the methods described above in reference to the example sensors of FIG. 1A. FIG. 4A is an illustrative graph of a base resonant response of an example resonator in accordance with at least some examples of the present disclosure. FIG. 4B is an illustrative graph of a shifted resonant response of an example resonator whose base resonant response is depicted in FIG. 4A. The horizontal axis corresponds to frequency, while the vertical axis corresponds to amount of resonance (e.g., amplitude or magnitude). As is illustrated in FIG. 4A, a base resonant frequency of a resonator may be determined based on a detection of a frequency corresponding to $f_0$. The base resonant frequency may correspond to the excited state of the resonator (e.g., when excited by an interrogation signal) in a vacuum or when a single base gas is present (e.g., where no particularly detectable gas of interest is present). FIG. 4B illustrates measured resonance frequencies (e.g., frequencies $f_1$ and $f_2$) of the resonator that may be found in response to the resonator being excited by an interrogation signal when exposed to two more gases (not including the base gas, if used). The presence of each gas may produce a frequency shift with respect to the base frequency (e.g., base resonant frequency $f_0$) of the resonator as indicated by frequencies $f_1$ and $f_2$. A first frequency shift may correspond to $f_2-f_0$, while a second frequency shift may correspond to $f_1-f_0$. The amplitude (or magnitude) of each corresponding frequency may correspond to amplitudes $R_1$ and $R_2$, respectively. By selecting nanotubes having a particular geometry, the resonant responses to plural gases may be more easily separated. That is, the resonance frequencies may be selected with a sufficiently high Q and narrow response frequency range that the resonant response associated with each gas may be more easily distinguished from resonant responses associated with other gases.

FIG. 5 is a block diagram of some example systems 500 for determining a concentration level of one or more gases in accordance with at least some examples of the present disclosure. The example system 500 may include an input/output interface 510 operatively coupled to a controller 520. A sensor interface 530 is also operatively coupled to the controller 520. The sensor interface 530 may be wired or wirelessly coupled to one or more sensors 540a, 540b, such as example sensors 100, 200, and 300 described above. The sensor interface 530 or measurement circuit 560 may include an oscillator (also referred to as a signal generator) configured to provide one or more interrogation signals to the one or more sensors 540. Each interrogation signal may include one or more associated frequencies as previously discussed. The oscillator may be configured to oscillate in response to a control signal from the controller 520.

In some examples, sensors 540 may be calibrated prior to use to detect a particular gas. In particular, a base resonance frequency of a resonator on a sensor 540 may first be obtained. For instance, a sensor 540 may be tested by exposing and measuring resonance characteristics of a resonator in a substantially constant and known gas for a period of time. While the resonator is exposed to the substantially constant and know gas, the gas molecules may associate with the nanotubes of the resonator. When the resonator resonates in response to the interrogation signal, a resonant response signal (e.g. a control response signal) may be generated in the feedline. A measurement circuit 560 measures one or more resonance characteristics of the resonator (e.g., resonance frequency of the resonator, Q-factor of the resonator, amplitude of the resonance response signal, phase of the resonance response signal, etc.) and may provide the measured values (i.e., the values indicative of the resonance characteristics) to a controller 520. The resonator may then be exposed to varying concentration levels of the same gas. At each concentration level, resonance characteristics of the resonator may be measured and stored. Based on these measured values a look-up table (LUT) or algorithm may be created to compare the measured resonance characteristics to those obtained previously for a known concentration level of the gas identified in the LUT or algorithm. For example, the controller 520 may be configured to access the LUT or algorithm based on a measured amplitude of a resonant frequency of the resonator to determine the concentration level of a gas detected by the sensor 540. In some examples, a sensor may be calibrated using another sensors calibration data. That is, once a first sensor has been calibrated as described above, the sensor's calibration data may be provided to the controller and used in combination with a second sensor having a second resonator thereon. The second sensor may be coupled to the controller. The controller may be configured to access the LUT or algorithm from the calibration data of the first sensor and detect a concentration level of a gas based on a measured amplitude of a resonance frequency of the second resonator.

The sensor interface 530 may be configured to receive a resonant response signal from the one or more sensors 540 indicating resonance of a resonator on a corresponding sensor 540 in response to an interrogation signal with a particular associated frequency (or range of frequencies). The resonant response signal may be operatively coupled to the controller 520. The system 500 may include a measurement circuit 560 configured to measure characteristics of the resonant response signal. For instance, the measurement circuit may be configured to measure an amplitude (or magnitude) of the resonant response signal. In some examples, the measurement circuit 560 may be configured to measure a frequency of the resonant response signal or a shift in the frequency with respect to the incident the interrogation signal. For instance, the measurement circuit 560 may include a frequency discriminator, such as a digital signal processing device. The system 500 may further include a memory circuit 570. The memory circuit 570 may be external to or internal to the controller 520. The memory circuit 570 may be configured to store the characteristics of the resonant response signal, such as the measured amplitude (or magnitude) of the resonant response signal. Additionally, the memory circuit 570 may store a LUT or algorithm as described above. The LUT or algorithm may be used to determine a concentration level of a gas detected by a sensor 540 based on the measured amplitude of the resonant response signal.

In one example, the measurement circuit 560 may receive the interrogation signal via a diode at a calibration port. The interrogation signal may be transmitted to the feedline via a diode such that the resonant response signal is not received by the calibration port of the measurement circuit 560. Beyond the interrogation signal diode, the resonant response signal is superimposed over the interrogation signal to form the measurement signal. The measurement circuit 560 receives the superimposed interrogation and resonant response signal at a measurement port. The measurement circuit 560 includes an inverter and an amplifier or attenuator that may be applied to either the calibration signal or the measurement signal. For simplicity, this description assumes the calibration signal is inverted and attenuated. The inverted and attenuated calibration signal is added to the measurement signal to form a filtered signal. The filtered signal thus includes only the resonant response signal, the interrogation signal being filtered out by the adder. The measurement circuit 560 includes a frequency analyzer operatively coupled to the filtered signal. The frequency analyzer outputs a digital waveform that represents the resonant behavior of the nanotube sensor. The controller 520 may use the digital waveform to address a LUT or as coefficients to an algorithm. The LUT or algorithm outputs one or more gas concentration levels, or a control signal corresponding to one or more gas concentration levels.

An identifier associated with a particular gas (e.g. a gas name) and a concentration level associated with the particular gas may be provided to the input/output interface 510. The input/output interface 510 may be operatively coupled to an audio and/or visual alarm or a processing unit configured to communicate to various external devices (e.g. such as a display, an air circulation unit, or speakers) via one or more ports.

In some examples, the controller 520 may be further operatively coupled to a control sensor, such as 540b, via the sensor interface 530. The control sensor 540b may be located in a different environment than a test sensor 540a. For instance, the control sensor 540b may be located in an environment in which concentration levels of one or more gases are not expected to change. The test sensor 540a may be located in an environment in which concentration levels of one or more gases are to be monitored. In response to an interrogation signal with a particular interrogation frequency provided to the sensors 540a and 540b by the sensor interface 530, a test resonant response signal may be generated by the test sensor 540a and a control resonant response signal may be generated by the control sensor 540b and provided back to the sensor interface 530. A difference may be determined between amplitudes (or magnitudes) of the control resonant response signal and the test resonant response signal. The controller 520 may be configured to access the LUT or algorithm to determine the concentration level of one or more detected gases based on the value of the difference in amplitudes between the two signals. When the differential between the signals is above a particular level (e.g., a threshold level), an indication signal may be generated and provided to an external device through the input/output interface 510. In this example, the accuracy of the measurement of the test resonant response signal is not necessary for a correct reading, since the concentration level of gas may be determined based on a differential between the two signals.

In some example systems, a comparator (not shown) or other similar device may be used to evaluate the resonant response signal instead of a LUT or algorithm, and a reference signal (either a single ended signal or a differential signal) can be employed to set a threshold level for the evaluation by the comparator. For example, a resonant response signal determined to be above the threshold level may be exhibited as a high output (e.g., logic 1) of the comparator and a resonant response signal determined to be below the threshold level may be exhibited as a low output (e.g., logic 0) of the comparator. Thus, the comparator may be used to compare the control resonant response signal with the test resonant response signal to detect whether a concentration level is above a particular level as set by the reference signal (e.g., a current of voltage signal). When the concentration level is determined to be high, an indication signal may be generated.

Figure 6:
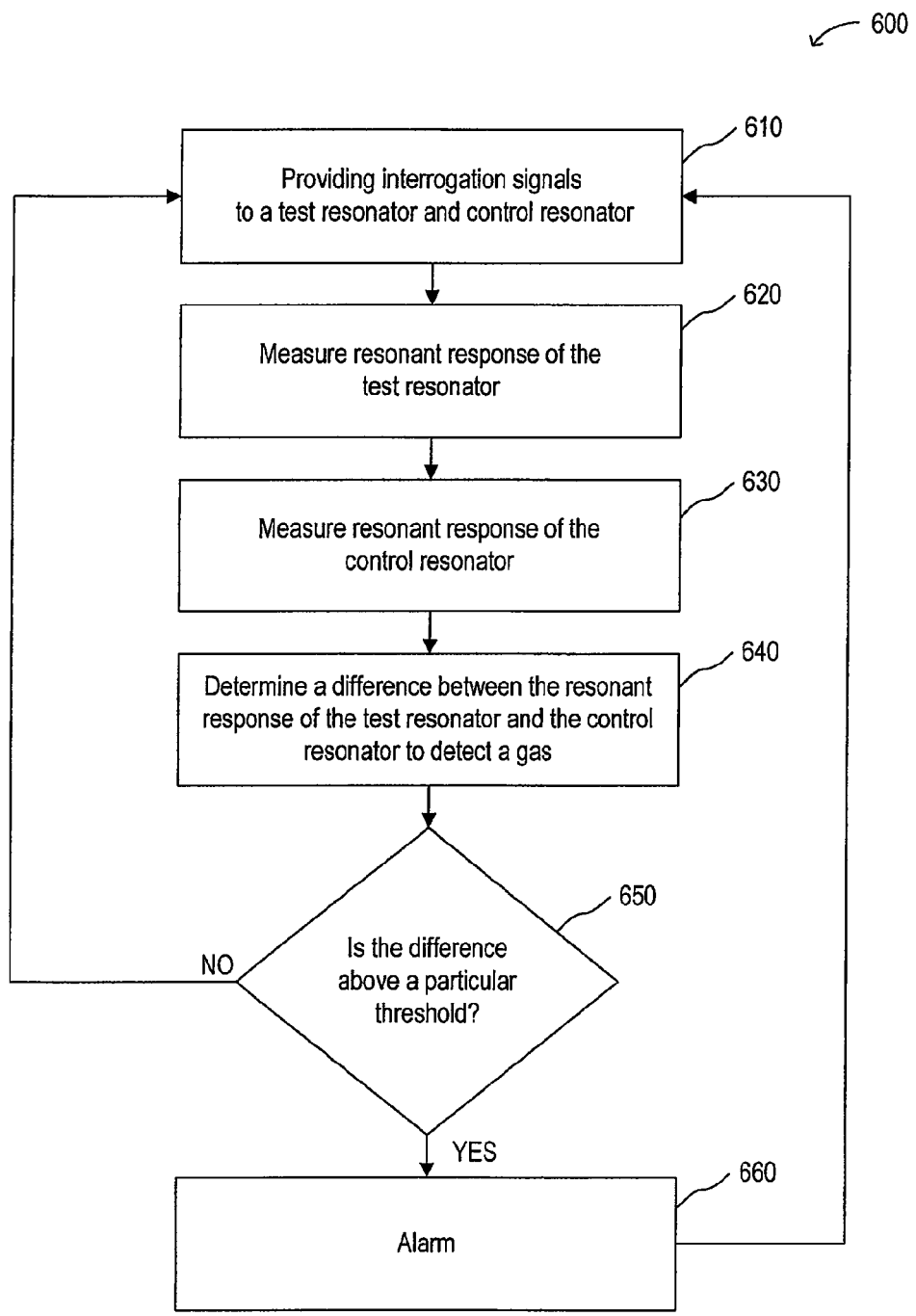
FIG. 6 is a flow chart illustrating some example methods for determining a concentration level of one or more gases

FIG. 6 is a flow chart illustrating some example methods 600 of detecting at least one gas in a volume including a mixture of two or more gases in accordance with at least some of the examples of the present disclosure. The method may include one or more functions, operations, or actions as illustrated by blocks 610-660. The example method may begin at block 610.

In block 610 interrogation signals may be provided (e.g., such as by a frequency source, an interrogation antenna, a feedline, or a combination thereof) to a resonator to be tested and to a control resonator.

Block 610 may be followed by block 620. In block 620, one or more test resonant response signals indicating resonance of the resonator to be tested may be detected and measured (e.g., such as by a measurement circuit, detector, controller, sensor interface or a combination thereof). Block 620 may be followed by block 630.

Block 630 is optional. In block 630, one or more control resonant response signals indicating resonance of a control resonator may be detected and measured (e.g., such as by a measurement circuit, controller, sensor interface, etc. or any combination thereof). Block 630 may be followed by block 640.

In block 640, a difference in amplitude between the test resonant response signal and the control resonant response signal may be obtained (e.g., such as by a controller that evaluates the difference between the resonant response signals, resonance characteristics, etc.), and an LUT or algorithm may be accessed to determine a presence and/or concentration level of one or more detected gases using the difference. Block 640 may be followed by block 650.

At block 650, the presence and/or concentration level of the one or more detected gases can be compared to a threshold (e.g., such as within a controller). If the presence and/or concentration level indicates the presence of one or more detected gases and/or the detected gas has a concentration level that is above the threshold, then block 650 may be followed by block 660 as is illustrated by the "YES" decision branch. If the presence and/or concentration level of the one or more detected gases is below the particular threshold then block 650 may be followed by block 610 as is illustrated by the "NO" decision branch.

At block 660, an alarm can be activated (e.g., an audible or visible alarm) or an alert can be issued to some other device to initiate an alarm condition or other corrective action. Block 670 may be followed by block 610.

The described and illustrated method 600 may be performed in an order or combination other than is illustrated and may include various blocks not shown. For instance, the tested resonator and the control resonator may be measured at the same time.

Figure 7:
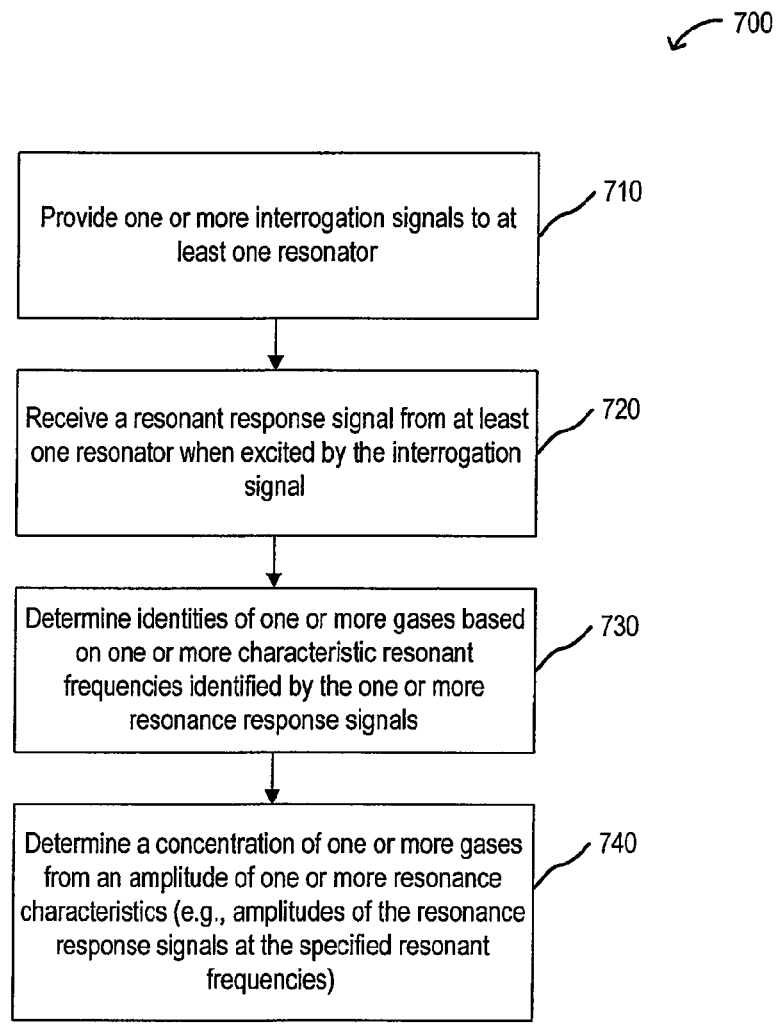
FIG. 7 is a flow chart illustrating some example methods for determining a concentration level of one or more gases.

FIG. 7 is a flow chart illustrating some example methods 700 of detecting at least one gas in a volume including a mixture of two or more gases in accordance with at least some of the examples of the present disclosure. The method may include one or more functions, operations, or actions as illustrated by blocks 710-740. The example method may begin at block 710.

In block 710, an interrogation signal may be provided (e.g., such as by a frequency source, an interrogation antenna, a feedline, or a combination thereof) to at least one resonator. Block 710 may be followed by block 720.

In block 720, one or more resonance characteristics (e.g., resonant frequency) of the at least one resonator may be measured (e.g. such as by the feedline, detector, measurement circuit, or a combination thereof). Block 720 may be followed by block 730.

In block 730, an identity of one or more gases may be determined as a function of one or more resonance characteristics (e.g., resonant frequency), such as by a LUT or algorithm as previously discussed above. Block 730 may be followed by block 740.

In block 740, a concentration of the gas may be determined from an amplitude of one or more resonance responses (e.g., amplitudes of the resonance response signals at the specified resonant frequencies), such as by a LUT or algorithm as previously described.

The described and illustrated method 700 may be performed in an order or combination other than is illustrated and may include various blocks not shown.

Figure 8:
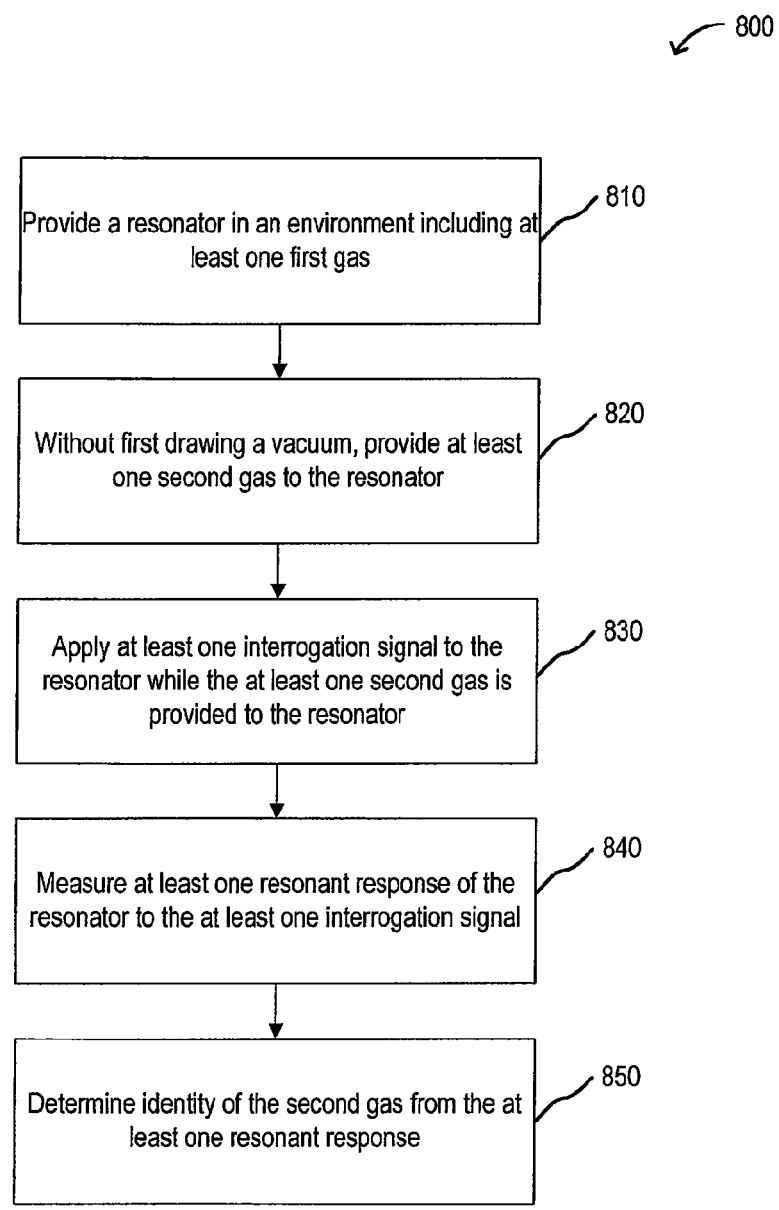
FIG. 8 is a flow chart illustrating some example methods 800 of detecting a change in a mixture including two or more gases.

FIG. 8 is a flow chart illustrating some example methods 800 of detecting a change in a mixture including two or more gases in accordance with at least some of the examples of the present disclosure. The method may include one or more functions, operations, or actions as illustrated by blocks 810-850. The example method may begin at block 810.

In block 810, a resonator may be provided in an environment including at least one first gas. Block 810 may be followed by block 820.

In block 820, without first drawing a vacuum, at least one second gas may be provided to the resonator. Block 820 may be followed by block 830.

In block 830, at least one interrogation signal may be applied to the resonator while the at least one second gas is provided to the resonator (e.g., such as by a frequency source, an interrogation antenna, a feedline, or a combination thereof). Block 830 may be followed by block 840.

In block 840, at least one resonant response of the resonator to the at least one interrogation signal may be measured (e.g. such as by the feedline, measurement circuit, detector, or a combination thereof). Block 840 may be followed by block 850.

In block 850, an identity of the second gas from the at least one resonant response may be determined, such as by a LUT or algorithm as previously discussed above The described and illustrated method 800 may be performed in an order or combination other than is illustrated and may include various blocks not shown.

Figure 9:
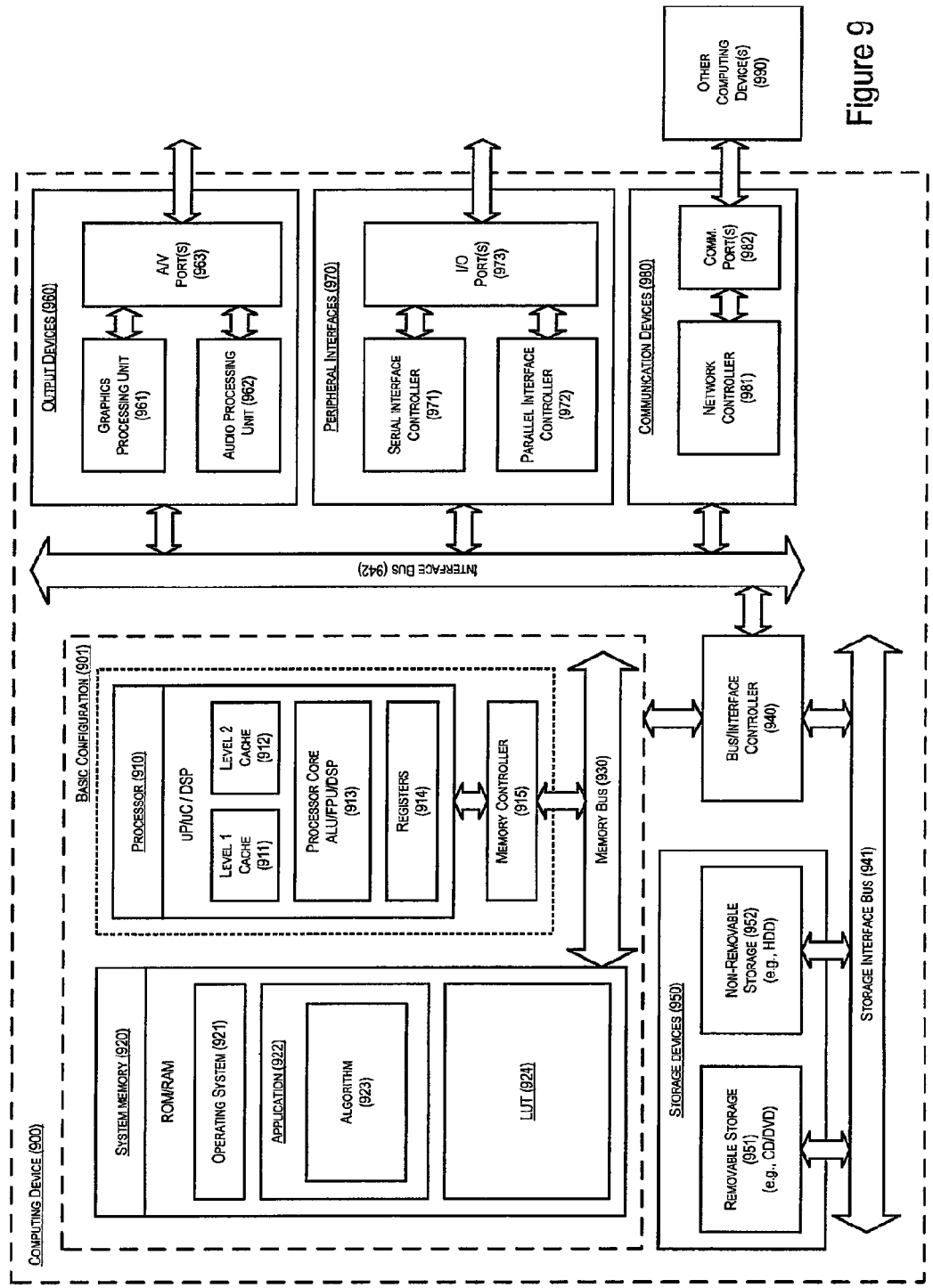
FIG. 9 is a block diagram illustrating some example computing devices; all arranged in accordance with at least some examples of the present disclosure.

FIG. 9 is a block diagram illustrating some example computing devices 900 that may be arranged for detecting one or more gases in accordance with at least some examples of the present disclosure. The computing device may be substituted for all or a portion of the input/output interface, the controller, and the sensor interface of FIG. 5. The computing device may be operatively coupled to any of the sensors 100, 200, and 300 in FIGS. 1-3. In a very basic configuration 901, computing device 900 typically may include one or more processors 910 and system memory 920. A memory bus 930 may be used for communicating between the processor 910 and the system memory 920.

Depending on the desired configuration, processor 910 may be of any type including but not limited to a microprocessor (µP), a microcontroller (µC), a digital signal processor (DSP), or any combination thereof. Processor 910 may include one more levels of caching, such as a level one cache 911 and a level two cache 912, a processor core 913, and registers 914. An example processor core 913 may include an arithmetic logic unit (ALU), a floating point unit (FPU), a digital signal processing core (DSP Core), or any combination thereof. An example memory controller 915 may also be used with the processor 910, or in some implementations the memory controller 915 may be an internal part of the processor 910.

Depending on the desired configuration, the system memory 920 may be of any type including but not limited to volatile memory (such as RAM), non-volatile memory (such as ROM, flash memory, etc.) or any combination thereof. System memory 920 may include an operating system 921, one or more applications 922, and program data 924. Application 922 may include an algorithm 923 configured to access an LUT to compare amplitudes of measured resonators. The application may be configured to receive signals indicative of a control measurement and a test measurement to detect a difference in accordance with the above described techniques. The application may be further configured to generate an indication signal when the difference is above a particular threshold. Program Data 924 may include an LUT including threshold levels for particular gases, such as amplitude threshold levels for measured resonance or differential thresholds for differences obtained from control and test sensors. In some embodiments, application 922 may be arranged to operate with program data 924 on an operating system 921 in accordance with one or more of the techniques, methods, and/or processes described herein. This described basic configuration is illustrated in FIG. 9 by those components within dashed line 901.

Computing device 900 may have additional features or functionality, and additional interfaces to facilitate communications between the basic configuration 901 and any required devices and interfaces. For example, a bus/interface controller 940 may be used to facilitate communications between the basic configuration 901 and one or more data storage devices 950 via a storage interface bus 941. The data storage devices 950 may be removable storage devices 951, non-removable storage devices 952, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 920, removable storage 951 and non-removable storage 952 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 900. Any such computer storage media may be part of device 900.

Computing device 900 may also include an interface bus 942 for facilitating communication from various interface devices (e.g., output interfaces, peripheral interfaces, and communication interfaces) to the basic configuration 901 via the bus/interface controller 940. Example output devices 960 include a graphics processing unit 961 and an audio processing unit 962, which may be configured to communicate to various external devices such as a display or speakers via one or more A/V ports 963. Example peripheral interfaces 970 include a serial interface controller 971 or a parallel interface controller 972, which may be configured to communicate with external devices such as input devices (e.g., keyboard, mouse, pen, voice input device, touch input device, etc.) or other peripheral devices (e.g., printer, scanner, etc.) via one or more I/O ports 973. An example communication device 980 includes a network controller 981, which may be arranged to facilitate communications with one or more other computing devices 990 over a network communication link via one or more communication ports 982.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 900 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 900 may also be implemented as a personal computer including both laptop computer and non-laptop computer configurations.

The present disclosure is not to be limited in terms of the particular examples described in this application, which are intended as illustrations of various aspects. Many modifications and examples can may be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and examples are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 items refers to groups having 1, 2, or 3 items. Similarly, a group having 1-5 items refers to groups having 1, 2, 3, 4, or 5 items, and so forth.

While the foregoing detailed description has set forth various examples of the devices and/or processes via the use of block diagrams, flowcharts, and/or examples, such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the examples disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. For example, if a user determines that speed and accuracy are paramount, the user may opt for a mainly hardware and/or firmware vehicle; if flexibility is paramount, the user may opt for a mainly software implementation; or, yet again alternatively, the user may opt for some combination of hardware, software, and/or firmware.

In addition, those skilled in the art will appreciate that the mechanisms of the subject matter described herein are capable of being distributed as a program product in a variety of forms, and that an illustrative example of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/ or quantities). A typical data processing system may be implemented utilizing any suitable commercially available components, such as those typically found in data computing/ communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A sensor configured to detect at least first and second gases in a volume that includes a mixture of two or more gases, the sensor comprising:
   a dielectric substrate;
   a first resonator on the dielectric substrate, the first resonator including:
      a first conductive plate on a first surface of the dielectric substrate; and
      a first nanotube layer arranged on the first conductive plate;
      wherein the first resonator has a first base resonant frequency selected to cause the first resonator to resonate in response to an interrogation signal when the first resonator is provided in contact with the first gas; and
   a second resonator on the dielectric substrate spaced apart from the first resonator along the first surface, the second resonator including:
      a second conductive plate on the first surface of the dielectric substrate; and
      a second nanotube layer arranged on the second conductive plate;
      wherein the second resonator has a second base resonant frequency different from the first base resonant frequency, the second base resonant frequency selected to cause the second resonator to resonate in response to the interrogation signal when the second resonator is provided in contact with the second gas.

2. The sensor of claim 1, wherein the interrogation signal is associated with an interrogation frequency, the first and second resonators configured to resonate in response to the interrogation frequency in the presence of the first and second gas, respectively.

3. The sensor of claim 1, wherein the first nanotube layer comprises a layer of nanotubes, nanotubes all having substantially a same size.

4. The sensor of claim 1, wherein the first conductive plate comprises a high aspect ratio rectangle or other polygon, the first resonator configured to generate a bi-modal resonant response.

5. The sensor of claim 1, wherein the first resonator and the second resonator have different sizes.

6. The sensor of claim 1, further comprising at least one feedline configured to provide the first interrogation signal to the first resonator and the second resonator, and wherein the interrogation signal has one or more frequencies associated therewith.

7. The sensor of claim 1, further comprising a first feedline configured to selectively provide the interrogation signal to the first resonator, and a second feedline configured to selectively provide the interrogation signal to the second resonator.

8. The sensor of claim 1, wherein at least one of the first conductive plate and the second conductive plate comprises one or more of a circular plate and/or a copper plate.

9. The sensor of claim 1, further comprising a ground plane insulated from and subjacent to the first resonator.

10. A system for detecting first and second gasses gases in a volume including a mixture of two or more gases, the system comprising:
 a signal generator configured to provide an interrogation signal;
 a sensor configured to receive the interrogation signal, wherein the sensor includes:
  a dielectric substrate;
  a first resonator including a first nanotube layer arranged on a first conductive plate disposed at a first location on the dielectric substrate, the first resonator configured to generate a first resonant response signal in response to the interrogation signal, the first resonant response signal being indicative of a resonance characteristic of the first resonator that changes when the sensor is in contact with the first gas in the volume such that the resonance characteristic of the first resonator identifies the first gas; and
  a second resonator including a second nanotube layer arranged on a second conductive plate disposed at a second location on the dielectric substrate spaced apart from the first location, and configured to generate a second resonant response signal in response to the interrogation signal, the second resonant response signal indicative of a resonance characteristic of the second resonator that changes when the sensor is in contact with the second gas in the volume such that the resonance characteristic of the second resonator identifies the second gas; and
 a detector configured to receive the first and second resonant response signals and generate a detection signal that indicates the resonance characteristic of the first resonator that identifies the first gas and/or the resonance characteristic of the second resonator that identifies the second gas.

11. The system of claim 10, wherein the signal generator and the detector are part of a sensor interface.

12. The system of claim 10, further comprising a controller that is operatively coupled to the detector and configured to receive the detection signal, wherein the controller is further configured to compare the detection signal with an expected value to determine the presence and/or absence of the first or second gas in the volume.

13. The system of claim 10, wherein the at least one sensor is wirelessly coupled to either the signal generator or the detector.

14. The system of claim 10, further comprising a control sensor including a control resonator, wherein the control sensor is located in a different volume including a known gas, wherein the control resonator is configured to generate a control response signal in response to another interrogation signal, the control response signal being indicative of a resonance characteristic of the control resonator when the control sensor is in contact with the known gas in the different volume such that the resonance characteristic of the control resonator identifies the known gas.

15. The system of claim 14, further comprising a controller configured to compare the resonance characteristics of the control resonator to the resonance characteristics of the first and/or second resonator to identify a difference indicative of the presence of the first and/or second gas about the first and/or second resonator, respectively.

16. The system of claim 15, wherein the identified difference corresponds to one or more of a difference in amplitude, a different in Q-factor, a difference in phase, a difference in resonant frequency, a shift in resonant frequency, and/or a difference in a plurality of resonant frequencies.

17. The system of claim 10, the first nanotube layer comprises a layer of first carbon nanotubes each having a first diameter and wherein the second nanotube layer comprises a layer of second carbon nanotubes each having a second diameter different from the first diameter, wherein the first resonator has a first resonant frequency when excited by the interrogation signal and the second resonator has a second resonant frequency when excited by the interrogation signal, and wherein the first resonant frequency shifts in the presence of the first gas and the second resonant frequency shifts in the presence of the second gas.

18. A method for identifying first and/or second gases in a volume including a mixture of two or more gases, the method comprising:
 applying an interrogation signal to a first resonator, the resonator including first carbon nanotubes arranged on a first conductive plate, the first conductive plate on a first surface of a dielectric substrate, the first resonator configured to associate with the first gas to generate a first shifted resonant response in response to the interrogation signal when the first resonator is exposed to the first gas;
 applying the interrogation signal to a second resonator separate from the first resonator, the second resonator including second carbon nanotubes arranged on a second conductive plate on the surface of the dielectric substrate, the second resonator configured to associate with the second gas to generate a second shifted resonant response in response to the interrogation signal when the second resonator is exposed to the second gas; measuring two or more resonant responses of the first resonator and the second resonator when excited by the interrogation signal, the two or more resonant responses including at least the first shifted resonant response and the second shifted resonant response; and
 identifying the first gas in the volume based on detecting the first shifted resonant response of the first resonator and identifying the second gas in the volume based on detecting the second shifted resonant response of the second resonator.

19. The method of claim 18, wherein
 the volume is a first volume, the method further comprising applying a control interrogation signal to a control sensor in contact with a second volume different from the first volume, measuring a control resonant response of the control sensor responsive to the control interrogation signal, and
 determining the identity of the first and/or second gases further based on detecting a difference between the control resonant response and at least one of the two or more resonant responses of the first resonator and the second resonator.

20. The method of claim 19, wherein the first resonator resonates at approximately the same time as the second resonator.

21. The method of claim 18, wherein the applying the interrogation signals to the first resonator comprises applying one or more first interrogation signals to a plurality of first resonators, and wherein the measuring two or more resonant responses further comprises measuring two or more first resonant responses of each first resonator of the plurality of first resonators.

22. A method for identifying a first gas and/or a second gas in a mixture including two or more gases, the method comprising:
receiving a radio based interrogation signal with an antenna that is operatively coupled to a first and second carbon nanotube resonators, the second carbon nanotube resonator havin a base resonant frequency that is different from a base resonant frequency of the first carbon nanotube resonator;
interrogating the first and second carbon nanotube resonators with the radio based interrogation signal;
generating at least one of a first resonant response and a second resonant response in response to the interrogating the first and second carbon nanotube resonators with the radio based interrogation signal, wherein the first resonant response of the first carbon nanotube resonator corresponds to a shifted resonant response of the first carbon nanotube resonator when exposed to the first gas, and wherein the second resonant response corresponds to a shifted resonant response of the second carbon nanotube resonator when exposed to;
identifying a presence of at least one of the first gas or the second gas in the mixture based on detecting the first resonant response or the second resonant response.

23. The method of claim 22, wherein at least a portion of the antenna includes the first and/or second carbon nanotube resonator.

24. The sensor of claim 1, wherein the first nanotube layer comprises nanotubes all having substantially a same first diameter.

25. The system of claim 10, wherein the first interrogation signal is different from the second interrogation signal.

26. The sensor of claim 1, wherein the sensor further comprises:
first and second feed lines operatively arranged to provide the interrogation signal to the first and second resonators, respectively; and
a switch configured to decouple the interrogation signal from the first feed line when coupling the interrogation signal to the second feed line, the switch being further configured to decouple the interrogation signal from the second feed line when coupling the interrogation signal to the first feed line.

27. The sensor of claim 3, wherein the second nanotube layer comprises a layer of nanotubes having a same size different than the size of the nanotubes of the first layer.

28. The sensor of claim 24, wherein the second nanotube layer comprises nanotubes all having a same second diameter different from the first diameter.

29. The sensor of claim 1, wherein at least one of the first nanotube layer and the second nanotube layer comprises a layer of nanotubes all having a same length.

30. The method of claim 18, wherein the first carbon nanotubes have a first diameter and the second carbon nanotubes have a second diameter different than the first diameter.

31. The method of claim 18, wherein the first carbon nanotubes have a first length and the second carbon nanotubes have a second length different than the first length.

32. The method of claim 22, wherein the radio based interrogation signal is associated with an interrogation frequency, and wherein the generating at least one resonant response signal comprises generating the first signal and the second signal in response to interrogating the first resonator and the second resonator, respectively, at the interrogation frequency.

33. The method of claim 22, wherein the base resonant frequencies of the first and second resonators are selected such that respective ones of the first and second resonators resonate at a same shifted resonant response when the respective ones of the first and second resonators are exposed to respective ones of the first and second gas.

* * * * *

UNITED STATES PATENT AND TRADEMARK OFFICE
CERTIFICATE OF CORRECTION

| | | |
|---|---|---|
| PATENT NO. | : 8,567,232 B2 | Page 1 of 1 |
| APPLICATION NO. | : 12/997859 | |
| DATED | : October 29, 2013 | |
| INVENTOR(S) | : Ackley et al. | |

It is certified that error appears in the above-identified patent and that said Letters Patent is hereby corrected as shown below:

In the Specification

In Column 1, Line 62, delete "gases" and insert -- gases. --, therefor.

In Column 6, Line 49, delete "detector 6." and insert -- detector 8. --, therefor.

In Column 9, Line 66, delete "light" and insert -- light; --, therefor.

In Column 17, Line 36, delete "above" and insert -- above. --, therefor.

In the Claims

In Column 22, Line 67, in Claim 6, delete "the first interrogation" and insert -- the interrogation --, therefor.

In Column 23, Line 13, in Claim 10, delete "gasses gases" and insert -- gases --, therefor.

In Column 25, Line 17, in Claim 22, delete "havin" and insert -- having --, therefor.

In Column 25, Line 32, in Claim 22, delete "exposed to;" and insert -- exposed to the second gas; --, therefor.

Signed and Sealed this
Seventh Day of October, 2014

Michelle K. Lee
*Deputy Director of the United States Patent and Trademark Office*